(12) United States Patent
Beyer et al.

(10) Patent No.: US 7,397,983 B2
(45) Date of Patent: Jul. 8, 2008

(54) LIGHT APPLICATOR AND METHOD FOR PRODUCING A DIFFUSER

(75) Inventors: Wolfgang Beyer, Gräfelfing (DE); Andreas Obermeier, München (DE)

(73) Assignee: Ludwig-Maximilians-Universtat of Munchen (DE)

( * ) Notice: Subject to any disclaimer, the term of this patent is extended or adjusted under 35 U.S.C. 154(b) by 0 days.

(21) Appl. No.: 10/511,378

(22) PCT Filed: Apr. 23, 2003

(86) PCT No.: PCT/DE03/01318

§ 371 (c)(1),
(2), (4) Date: Jul. 12, 2005

(87) PCT Pub. No.: WO03/090866

PCT Pub. Date: Nov. 6, 2003

(65) Prior Publication Data

US 2005/0271346 A1    Dec. 8, 2005

(30) Foreign Application Priority Data

Apr. 24, 2002 (DE) .......................... 202 06 473 U
Nov. 29, 2002 (DE) .............................. 102 56 139

(51) Int. Cl.
G02B 6/26 (2006.01)
G02B 6/00 (2006.01)
(52) U.S. Cl. .......................... 385/28; 385/18; 385/140
(58) Field of Classification Search .................. 385/28, 385/18, 140
See application file for complete search history.

(56) References Cited

U.S. PATENT DOCUMENTS

| 4,422,719 | A | * | 12/1983 | Orcutt ........................ 385/123 |
| 5,051,872 | A | * | 9/1991 | Anderson .................... 362/558 |
| 5,059,191 | A | | 10/1991 | Beyer et al. |
| 5,196,005 | A | * | 3/1993 | Doiron et al. .................. 606/7 |
| 5,219,346 | A | | 6/1993 | Wagnières et al. |
| 5,269,777 | A | | 12/1993 | Doiron et al. |
| 5,695,583 | A | * | 12/1997 | van den Bergh et al. .... 156/153 |
| 5,908,415 | A | | 6/1999 | Sinofsky |
| 5,957,917 | A | | 9/1999 | Doiron et al. |
| 5,978,541 | A | | 11/1999 | Doiron et al. |
| 6,270,492 | B1 | | 8/2001 | Sinofsky |
| 6,423,055 | B1 | | 7/2002 | Farr et al. |

(Continued)

FOREIGN PATENT DOCUMENTS

DE    3901931    8/1990

(Continued)

OTHER PUBLICATIONS

Bayer Jurnal of photochemistry and Photography B: Biology, 36 (1996) 153-156.*

(Continued)

*Primary Examiner*—Kianni C Kaveh
(74) *Attorney, Agent, or Firm*—Bolesh J. Skutnik; BJ Associates

(57) ABSTRACT

A light applicator (27) for medical applications is proposed whose diffusor (1) comprises diffusion regions (7, 8, 9) with paraboloidal boundary surfaces (11, 12) This configuration of the diffusor (1) permits a particularly good homogenization of the distribution of light along the longitudinal axis of the diffuser (1).

23 Claims, 4 Drawing Sheets

U.S. PATENT DOCUMENTS

| | | | |
|---|---|---|---|
| 2002/0007111 A1* | 1/2002 | Deckert et al. | 600/177 |
| 2002/0027626 A1* | 3/2002 | Hiraishi et al. | 349/112 |
| 2004/0005423 A1* | 1/2004 | Dalton et al. | 428/36.9 |
| 2005/0165462 A1* | 7/2005 | Bays et al. | 607/88 |

FOREIGN PATENT DOCUMENTS

| | | |
|---|---|---|
| DE | 3909843 | 9/1990 |
| EP | 0 437 183 | 7/1991 |
| EP | 0 439 629 | 8/1991 |
| GB | 2 227 333 | 7/1990 |
| WO | WO 94/17434 | 8/1994 |

OTHER PUBLICATIONS

Forscungsberich 97 (Entwichlung eines Lichtapplikators fur die PDT von Portio und Zervixkanal), Feb. 1997.*

International Search Report, Dec. 10, 2003, PCT/DE 03/01318.

"Entwicklung eines Lichtapplikators für die PDT von Portio und Zervix-Kanal", in: Laser- und Immunologie-Forschungseinrichtungen (LIFE), Urologische Klinik und Poliklinik, Ludwig-Maximilians-Universität, Forschungs-bericht 1997, p. 17, http://laser.klinikum.uni-muenchen.de/Fb97/Zervixapp.htm (in German—discloses a light applicator similar to the light applicator claimed in the International Patent Application but without paraboloidal boundary surfaces of the diffusion regions).

W. Beyer, "Systems for light application and dosimetry in photodynamic therapy," Journal of Photochemistry and Photobiology B: Biology 36 (1996), pp. 153-156.

* cited by examiner

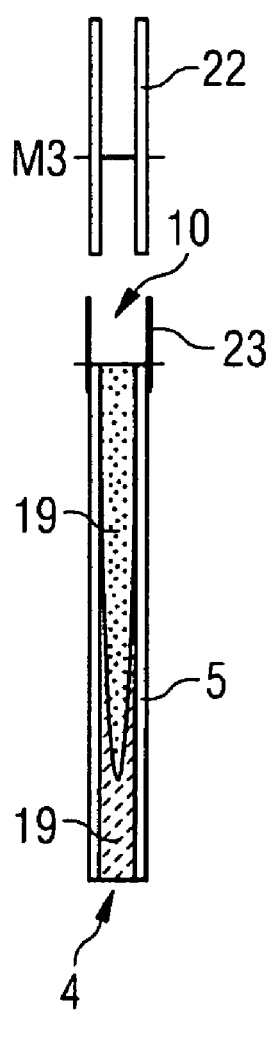
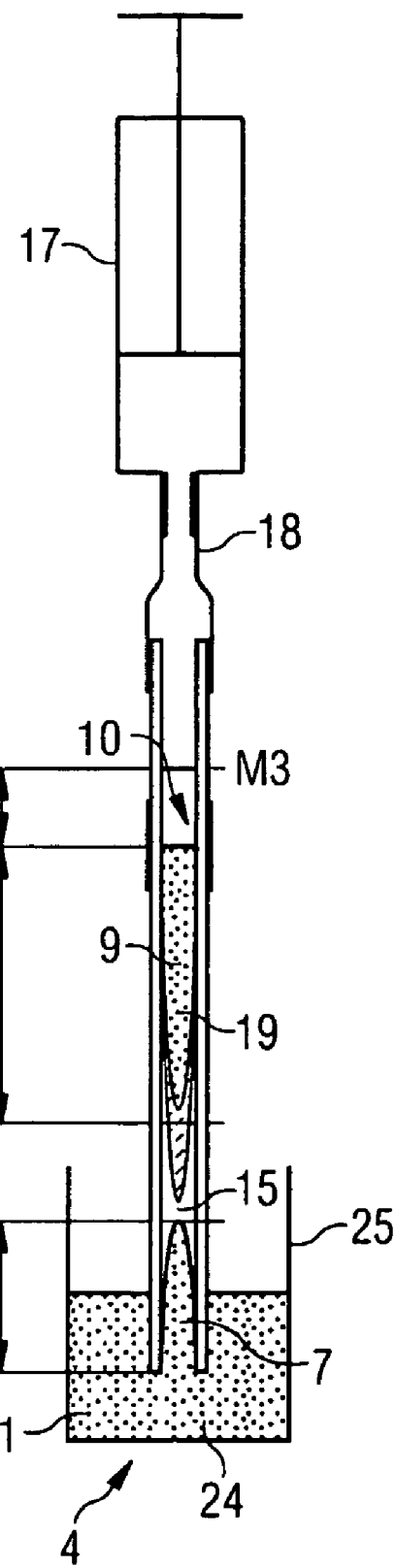

LIGHT APPLICATOR AND METHOD FOR PRODUCING A DIFFUSER

CROSS-REFERENCE TO RELATED APPLICATIONS

This application is a US National Stage of International Application No. PCT/DE03/01318 filed 23 Apr. 2003. This application claims the benefit of German Application Nos. 202 06 473.5, filed 24 Apr. 2002 and 102 56 139.7, filed 29 Nov. 2002. The disclosure(s) of the above applications are incorporated herein by reference.

The invention relates to a light applicator with a diffusor which is attachable to a light guide and in which different diffusion regions with different scattering parameters follow successively along an optical axis of the light guide prolongated into the diffuser.

The invention further relates to a method for producing a diffusor connectable to a light guide.

Such a light applicator for medical applications and a method for producing a diffusor attachable to a light guide is known from U.S. Pat. No. 5,978,541. The known light applicator comprises a cylindrical core which is interspersed with light scattering particles. The light scattering particles are used as scattering centers at which the light arriving through the light guide in the diffusor is scattered.

The distribution of concentration of the scattering centers along the optical axis of the light guide connectable to the diffusor, which axis is prolongated into the diffuser, is chosen in such a way that the diffusor emits light with a predetermined light distribution.

The diffusor is produced in an extrusion process in which the concentration of the scattering centers is set by mixing two suspensions with different concentrations. The concentration of the scattering centers during the extrusion process is continuously monitored for the purpose of producing a specific concentration profile and is compared with a predetermined set value.

For the determination of the set values it is proposed to assemble prototypes of the diffusor from individual parts with different concentrations. It is then possible from the plurality of prototypes to choose the one prototype whose light distribution corresponds best to the desired light distribution. The mixing process during the extrusion of the diffusor is then set in such a way that the finished diffusor then shows approximately the desired distribution of the scattering centers.

The known light applicators are generally used within the scope of photodynamic therapy for the treatment of tumors. A photosensitizer which enriches selectively in the tumor is applied in this process. After the application of the photosensitizer the tumor and the ambient healthy tissue is irradiated with light. Toxins are produced through the thus initiated photochemical processes which damage the tumor in a purposeful manner as a result of the tumor selectivity.

Since a certain concentration of the photosensitizer (although a low one) will set even in the healthy tissue, any overdosing with light may lead to undesirable tissue damage in the healthy tissue. On the other hand, the desired therapeutic success will not to be achieved in the case of under-dosage. The tolerance range for the light dose to be applied is therefore often narrow. Since the light distribution depends on the distribution of the scattering centers, a certain distribution of concentration of the scattering centers in the diffusor is necessary for a specific light distribution. In order to ensure that the required precision in the concentration of the scattering centers can be achieved, the known method for producing the diffusor requires a complex regulation for the extrusion process.

On the basis of this state of the art, the invention is therefore based on the object of providing an easy-to-produce light applicator and a method for producing a diffusor which can be used for the light applicator and offers a defined distribution of concentration of the scattering centers.

These objects are achieved by the light applicator and the method with the features of the independent claims. Further embodiments and refinements are subject matter of the dependent claims.

The diffusor is configured in the light applicator in such a manner that the diffusion regions will overlap with respect to a line-of-sight aligned at a right angle to the optical axis of the light guide. In the overlapping region of the diffusion regions, a cross-sectional surface whose normal is the optical axis is therefore composed of partial surface areas with different scattering parameters. The light incident along the optical axis will therefore meet different partial surface areas with different scattering parameters. The surface area ratio of the diffusion regions in the respective cross-sectional surface can be chosen according to the desired light intensity. In the light applicator there is accordingly not a mixing process of the different diffusion mediums in production, but a mixture of the fractions of light scattered in the various diffusion regions.

Since the diffusion regions comprising different scattering parameters are separated, the scattering parameters of the individual diffusion regions can be separately set during the production with a high amount of precision to the required values. For the production of the diffusor for the light applicator it is especially not necessary to perform and monitor a complex mixing process. The diffusion media for the different diffusion regions with the different scattering parameters can rather be produced separately and joined together to the common diffusor. The light applicator can thus be produced in a simple manner such that a predetermined emission profile is maintained.

In a preferred embodiment of the light applicator, the boundary surfaces are provided with a paraboloidal configuration, with the axes of symmetry of the paraboloids extending along the optical axis of the light guide wherein the optical axis is prolongated into the diffusion medium. Since the cross-sectional surface area of the paraboloids change in a linear way along the path covered along the optical axis, this configuration allows a linear transition between two diffusion regions with different scattering parameters. Moreover, the diffusion regions can be produced by injecting a first diffusion medium into a second diffusion medium, with injection being understood both as suction as well as injection.

In a further preferred embodiment of the invention, a reflector is associated with a proximal end of the diffusor which guides the light emitted from the diffusor in predetermined directions. Such a reflector can be a scattering hemisphere which guides the light emitted by the diffusor towards the distal end. Such a light applicator is especially suitable within the scope of gynecology for the photodynamic therapy of dysplasia on the surface of portio and cervical canal.

The invention is now explained in closer detail by reference to the enclosed drawings, wherein:

FIGS. 4a to 4e shows representations of the method steps applied to produce the diffusor of FIG. 2;

Figure 1:
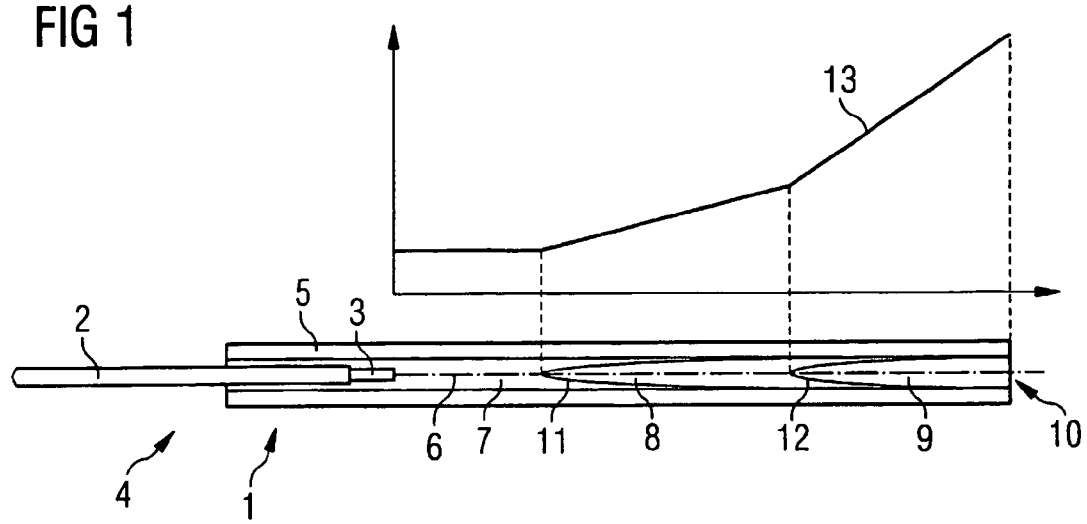
FIG. 1 shows a cross-sectional view through a first embodiment of a diffusor and a diagram with the concentration of the scattering centers in the diffusor as averaged over the cross section.

The diffusor 1 as shown in FIG. 1 can be connected to a light guide 2. The light guide 2 projects with a light guide fiber 3 into the proximal end 4 of a tube section 5. FIG. 1 shows an optical axis 6 of the light guide fiber 3 extended into the interior of the tube section 5.

Along the optical axis 6 which is prolongated into the interior of the tube section 5, a proximal diffusion region 7, a medium diffusion region 8 and a distal diffusion region 9 are successively formed. The distal diffusion region 9 closes off a distal end 10 of the tube section 5. The proximal diffusion region 7, the middle diffusion region 8 and the distal diffusion region 9 are each mutually delimited by paraboloidal boundary surfaces 11 and 12. In the embodiment of the diffusor 1 as shown in FIG. 1, the paraboloid apexes of the paraboloidal boundary surfaces 11 and 12 each face the proximal end 4 of the diffusor 1. Moreover, the axes of symmetry of the paraboloidal boundary surfaces 11 and 12 are situated on the optical axis 6. Since the cross-sectional surfaces of the paraboloidal boundary surfaces 11 and 12 which are aligned at a right angle to the optical axis 6 are proportional to the distance from the paraboloid apex, the concentration of the scattering centers which is averaged with respect to surface area over the cross-sectional surface area increases or decreases in a linear manner with the distance from the paraboloid apex of the paraboloidal boundary surfaces 11 and 12 depending on the concentration of the scattering centers in the proximal diffusion region 7, the middle diffusion region 8 and the distal diffusion region 9.

The concentrations of the scattering centers in the proximal diffusion region 7, in the middle diffusion region 8 and in the distal diffusion region 9 are designated below with $c_1$, $c_2$ and $c_3$. The concentrations of the scattering centers in the proximal diffusion region 7, in the middle diffusion region 8 and in the distal diffusion region 9 can assume highly different values.

The linear transition of the surface portions of the different diffusion regions 7, 8 and 9 leads to a concentration curve 13, as is shown by way of example in the diagram shown in FIG. 1. In the diagram as shown in FIG. 1, the path along the optical axis 6 is entered along the ordinate. The abscissa shows the concentration of the diffusion regions 7 through 9 as averaged over the cross-sectional surface area.

When the concentration of the scattering centers rises from the proximal diffusion region 7 to the distal diffusion region 9, meaning that $c_1<c_2<c_3$ applies, the concentration curve 13 of the scattering centers is obtained which is shown in FIG. 1 and which is linear in sections and rises continually. The scattering probability therefore increases from the proximal end 4 to the distal end 10. The intensity of the light which extends along the optical axis 6 and decreases from the proximal end 4 to the distal end 10 can be compensated with the help of the concentration curve 13. As a result, the intensity of the light scattered out of the diffusor 1 will hardly decrease from the proximal end 4 to the distal end 10. A homogeneous distribution of light along the optical axis 6 can thus be achieved. A homogeneous distribution of light shall preferably be understood as a distribution of light in which the power density on the light-emitting surfaces of the diffusor fluctuates by a maximum of +/−15%, preferably +/−10%.

Figure 2:
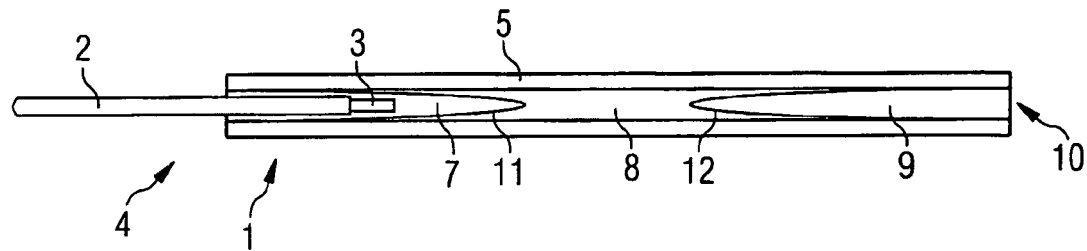
FIG. 2 shows a cross section through a further modified diffusor.

In FIG. 1, the paraboloidal apex of the paraboloidal boundary surfaces 11 and 12 each face the proximal end 4 of the diffusor 1. This is not mandatory. FIG. 2 shows a modified embodiment of diffusor 1 in which the boundary surface 11 between the proximal diffusion region 7 and the middle diffusion region 8 is a paraboloid whose paraboloid apex faces the distal end 10. This configuration of the diffusion regions 7 through 9 allows producing concentration curves which cannot be produced with similarly directed orientation of the diffusion regions 7 to 9. For example, the middle diffusion region 8 of the diffusor 1 as shown in FIG. 2 can be free from scattering centers, so that a characteristic minimum is obtained in the concentration profile of the scattering centers.

Figure 3:
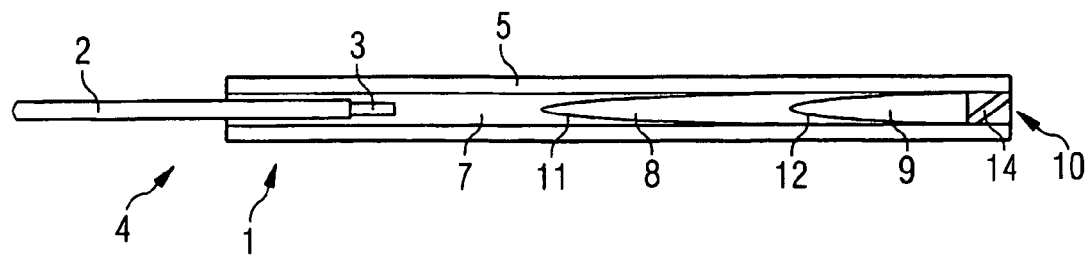
FIG. 3 shows a cross section through a diffusor whose distal end is closed off with a mirror.

FIG. 3 shows a further modified embodiment of the diffusor 1 in which a mirror 14 is introduced into the tube section 5 at the distal end 10 of the diffusor 1. The exit of light at the distal end of the diffusor 1 is prevented by the mirror 14.

FIGS. 4a through 4e show successive method steps for producing the diffusor 1 shown in FIG. 2.

The diffusion regions 7 through 9 in the tube section 5 are generally formed in such a way that a curable, liquid diffusion medium to which scattering particles are admixed is introduced into the tube section 5.

Prior to the filling of the tube section 5, markings M1 and M2 are applied to the tube section 5. The markings M1 and M2 are arranged at a distance $L_{E3}=20$ mm. Since the cross-sectional surface area of a paraboloid increases proportional to the distance from the paraboloid apex, the volume of a paraboloid is equal to the cross-sectional surface area multiplied by half the distance from the paraboloid apex, or in other words equal to the base area multiplied by half the height of the paraboloid. The volume marked with the markings M1 and M2 in the tube section 2 corresponds to the volume of a diffusion medium to be sucked into the tube section 5 with the height $L_{P3}=40$ mm.

At first, however, a first diffusion medium 15 provided for the middle diffusion region 8 is sucked into the tube section 5 from a container 16 up to the marking M1. A suction pump 17 is used for sucking the diffusion medium 15 into the tube section 5, which pump is connected via a tube section 18 with the proximal end 4 of the tube section 5.

Prior to the curing of the medium 15, a further diffusion medium 19 which is provided for the distal diffusion region 9 is sucked into the tube section 5 from a container 20. As a result of the laminar flow of the diffusion medium 19, the diffusion medium 19 progresses further into the diffusion medium 15 in the middle region of the tube section than at the edge. The paraboloidal boundary surface 12 is thus formed between the distal diffusion region 9 and the middle diffusion region 8. When the diffusion medium 19 is sucked into the tube section 5, the air-fluid-level of the diffusion medium 15 is lifted from the marking M1 to the marking M2. This leads to a distal diffusion region 9 whose volume corresponds to the volume of the tube section 5 situated between the markings M1 and M2. The length $L_{P3}$ of the distal diffusion region 9 is therefore twice the distance $L_{E3}$ between the markings M1 and M2. By sending light into the diffusion media 15 and 19 it is possible to check the diffusion media 15 and 19 which are sucked into the tube section 5 for the absence of bubbles and to check the boundary surface 12 for flawless formation.

Figure 4A:
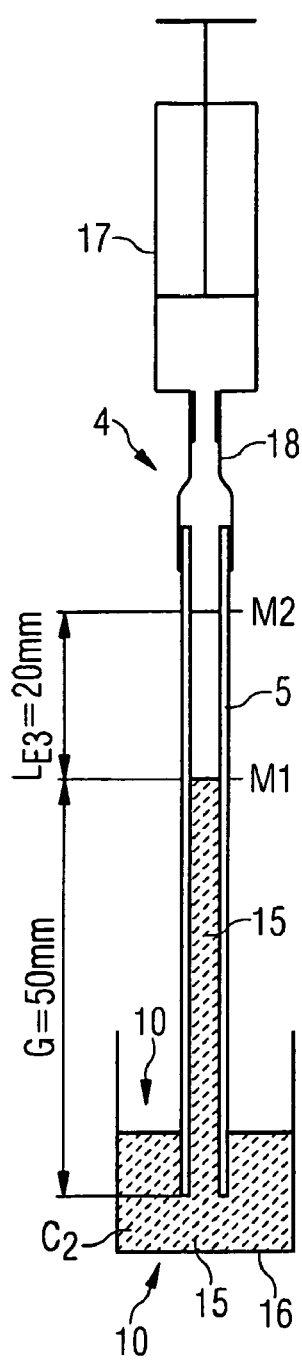
Figure 4B:
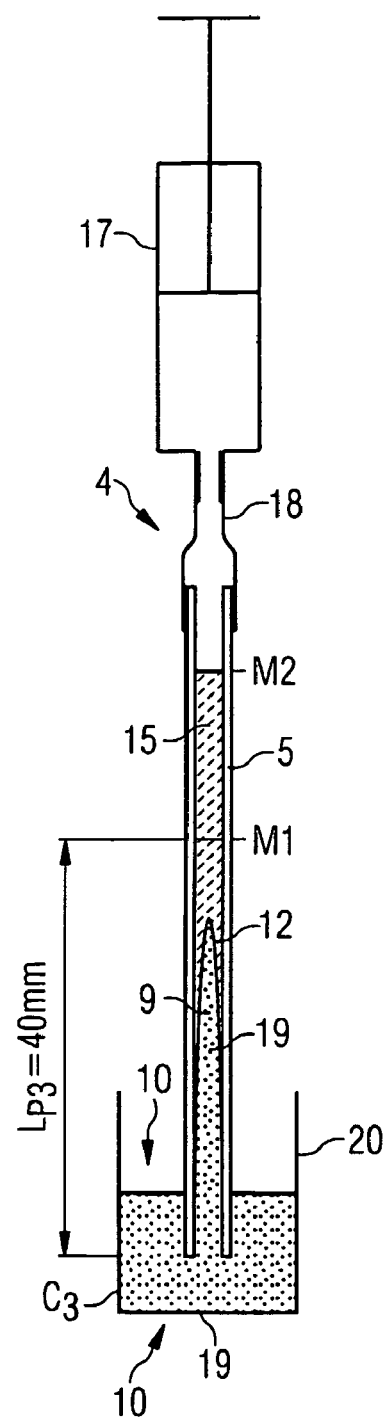
Figure 4C:
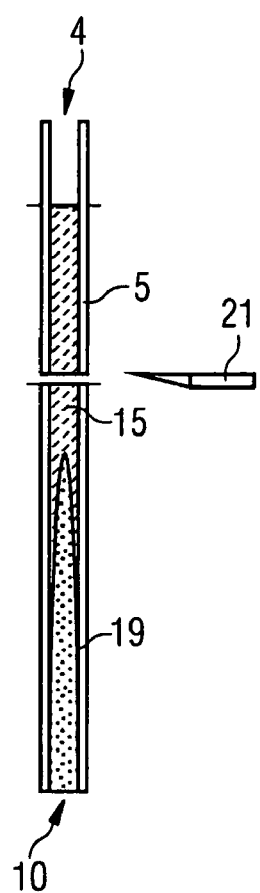

Finally, the tube section 5 is cut to the total length of $G=50$ mm with the help of a cutting apparatus 21 in accordance with FIG. 4c. In a further method step as shown in FIG. 4d, the tube section 5 is twisted by 180° and an extension portion 22 is attached to the distal end 10 with the help of a connection piece 23. The extension portion 22 is provided with a marking M3 which is situated at a distance $L_{E1}=8$ mm from the end of the tube section 5. The marking M3 marks the suction length for forming the proximal diffusion region 7. It is produced in such a way that according to FIG. 4e from the proximal end 4 of the tube section 5 a diffusion medium 24 intended for the proximal diffusion region 7 is sucked in from a container 25. The paraboloidal distal diffusion region 9 moves back to the marking M3.

In further method steps (not shown), the distal end 10 is sealed by the mirror 14 and the light guide 2 is introduced into the proximal end 4 of the diffusor 1 and the diffusion media 15, 19 and 24 are cured. The light guide fiber 3 is fixed in the proximal diffusion region 7.

The diffusers 1 illustrated in the FIGS. 1 to 3 can be used in the present form as light applicators for irradiating hollow organs. The diffusers 1 can also be further modified for special applications.

Figure 5:
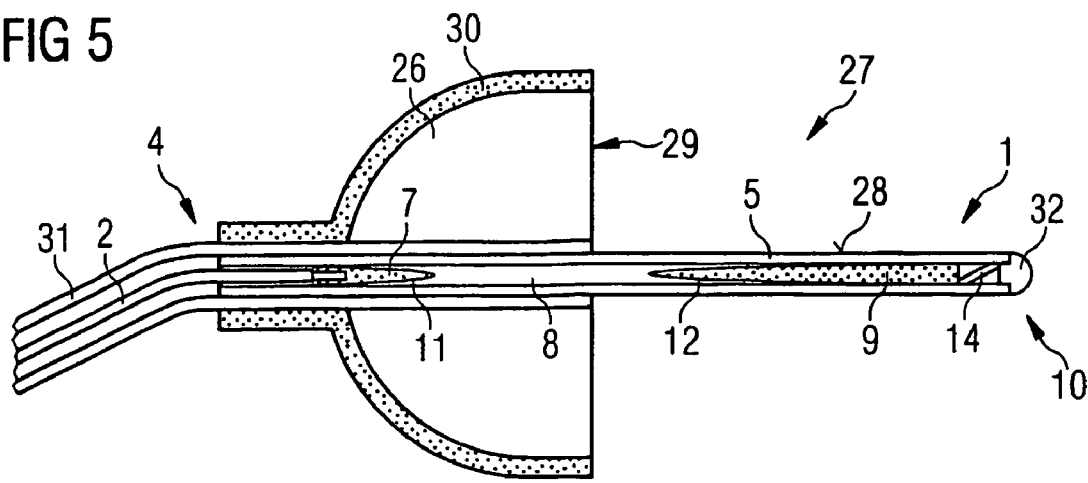
FIG. 5 shows a cross section through a light applicator for portio and cervical canal.

The diffusers 1 can be used in gynecology as light sources for irradiating portio and cervical canal. For this purpose the diffusor of FIG. 2 (as shown in FIG. 5) is combined with a transparent hemisphere 26 which is arranged at the proximal end 4 of the diffusor 1. In combination with the hemisphere 26, the diffusor 1 forms a light applicator 27 whose light exit surface is formed by a tube surface 28 of the tube portion 5 and a cross-sectional hemisphere surface 29 of the hemisphere 26. In order to prevent any undesirable irradiation of the vaginal wall, the rear-side surface of the hemisphere 26 is provided with a reflective or completely retroreflective reflection layer 30.

The hemisphere 26 does not sit directly on the diffusor 1. The diffusor 1 is embedded in a transparent tube 31 which for anatomical reasons is bent at an angle of approximately 30° directly after the hemisphere 26. A handle is attached to tube 31 (not shown in FIG. 5) which the physician can use to manipulate the light applicator 27. In order to eliminate any likelihood of injury, the distal end 10 of the diffusor 1 is closed off by a round cap 32.

In the embodiment as shown in FIG. 5, the concentration of the scattering centers in the proximal diffusion region 7 and in the distal diffusion region 9 is higher than in the middle diffusion region 8. The concentration of the scattering centers therefore decreases from the proximal end 4 to the middle diffusion region 8 and increases again towards the distal end 10. A strong radiation from the diffusor 1 in the region of the hemisphere 26 is achieved through this choice of the concentration conditions. The hemisphere 26 is supplied by the proximal diffusion region 7 with light. The distal diffusion region 9 ensures on the other hand that a sufficient quantity of light emerges from the tube surface 28. Since the concentration of the scattering centers averaged over the cross section of the diffuser 1 increases towards the distal end 10 of the diffusor 1, the drop in the incident light along the optical axis 6 is compensated. By making a suitable choice of the concentration in the distal diffusion region 9 and in the middle diffusion region 8, a homogeneous distribution of light can be achieved over the diffusor 1. The homogeneous distribution of light over the cross-sectional hemisphere surface 29 is further ensured by the reflection layer 30 if a retroreflective material is used for the reflection layer 30.

In order to improve the contact with the tissue to be irradiated between portio and cervical canal, the shape of the surface of the hemisphere 26 can be adjusted to the anatomy. For this purpose the modified embodiment of the light applicator 27 as shown in FIG. 6 is provided with a conical nose 33 which is attached to the cross-sectional hemisphere surface 29 and tapers towards the distal end 10.

Figure 7:
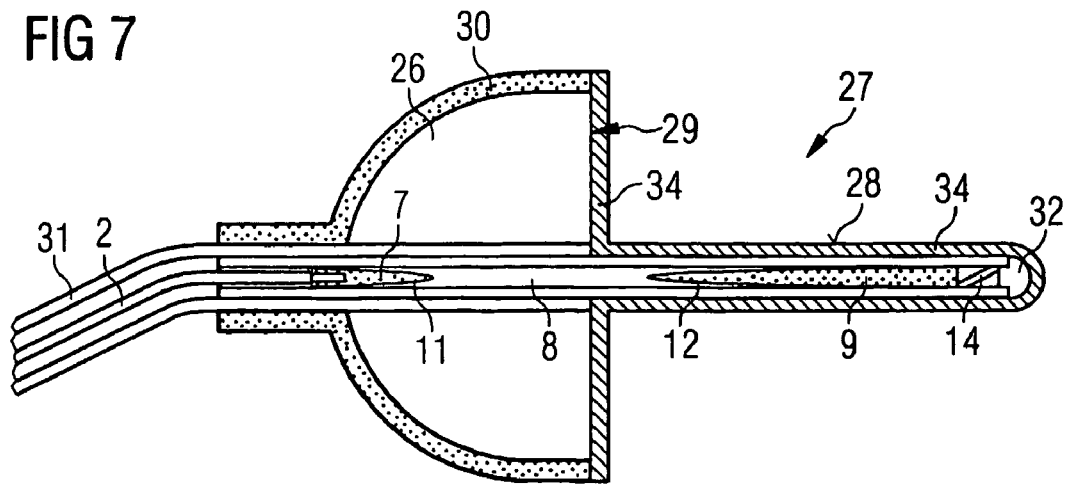
FIG. 7 shows cross-sectional view through a light applicator whose light exit surface is provided with a partially backscattering layer.

In order to further improve the spatial homogeneity of the radiation emerging from the light applicator 27, the light exit surface which is formed by the tube surface 28 and the cross-sectional hemisphere surface 29 can be provided, as shown in FIG. 7, with a partially backscattering layer 34. If the reflectivity of the backscattering layer 34 is higher than its transparency, the photons are scattered back on average several times into the interior of the diffusor 1 and the hemisphere 26 before they finally leave the light applicator 27 through the backscattering layer 34. In this way, the spatial distribution of light in the interior of the light applicator 27 is homogenized and thus also the distribution of the light emitted to the outside by the backscattering layer 34.

Figure 6:
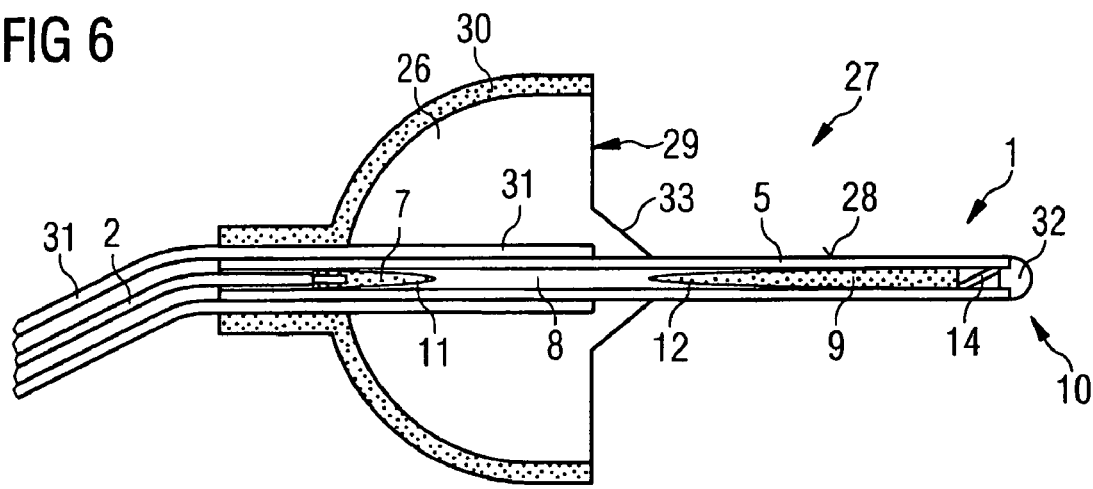
FIG. 6 shows a cross-sectional view through a further modified light applicator.

It is to be noted that a layer corresponding to the backscattering layer 34 can also be applied to the embodiment of the light applicator 27 as shown in FIG. 6.

A suitable material for the diffusion media in the diffusion regions 7, 8, and 9 is a highly transparent silicone caoutchouc which can be doped with $TiO_2$ or $BaSO_4$. A mixture ready for processing made of 50% coloring pigments on the basis of $TiO_2$ and 50% carrier material on the basis of silicone caoutchouc is the material RTV-ME 601 with the paste FL White of the company Wacker in Burghausen. This material can be further diluted with clear silicone caoutchouc until the desired concentrations are achieved. The concentrations of the paste FL White for the diffusor 1 with a length of 5 cm lie in the magnitude of 0.005% to 0.2%. At higher concentrations of the scattering centers, this material can also be used for the backscattering layer 34 or the reflection layer 30. Moreover, this material can be processed in the liquid state and cures at room temperature after a typical curing time of 90 minutes.

A material should be used as a material for the tube portion 5 whose refractive index is smaller than the refractive index of the diffusion medium used for the diffusion regions 7 through 9. In this case, especially the non-scattered light at the boundary surface between the tube portion 5 and the diffusion regions 7 through 9 are totally reflected until it meets the boundary surface after a scattering event under an angle which allows the passage of the scattered light. This ensures that non-scattered light does not leave the diffusor 1.

If the diffusor 1 needs not to be flexible, it is possible to use a tube made of plexiglass instead of the tube portion 5.

A silver cylinder with a polished end surface or a short glass fiber element whose proximal end surface was vaporized with silver may be used for the mirror 14 at the distal end 10 of the diffusor 1. Other materials adjusted to the wavelength of the used light such as aluminum can also be used for forming the mirror surface.

The essential advantages of the light applicators as described herein are the minor efforts in the production of the diffusor 1 and the high amount of freedom in the design of the distribution of the light as emitted by the light applicators. It is especially possible to achieve a homogeneous distribution of light along the diffusor 1. By combining the diffusor 1 with the hemisphere 26 a light applicator 27 is obtained which substantially simplifies the photodynamic therapy of portio and cervical canal. The irradiation of portio and cervical canal can now occur in one pass without any cumbersome positioning and dosimetric calculations with direct tissue contact.

As was already mentioned, the light applicators as described herein can be used for photodynamic therapy (PDT). In addition, a use within the scope of photodynamic diagnosis (PDD) and laser-induced thermotherapy (LITT) can be considered.

Finally it is to be noted that the paraboloidal boundary surfaces can also be replaced by boundary surfaces which are conical or have the shape of a truncated cone, are hyperboloidal or following the progress of an exponential function. The boundary surfaces need not necessarily be configured in a rotationally symmetrical way relative to the longitudinal axis of the diffusor. However, the individual diffusion regions should overlap along a line-of-sight oriented at a right angle to the longitudinal axis of the diffusor in order to allow a gradual transition from one diffusion region to the adjacent diffusion region.

The invention claimed is:

1. A light applicator with a diffusor which is attachable to a light guide and in which different diffusion regions with different scattering parameters follow successively along an optical axis of the light guide prelongated into the diffusor and in which the diffusion regions will overlap with respect to a line-of-sight aligned at a right angle to the optical axis of the light guide, wherein a boundary surface between adjacent diffusion regions has the shape of a laminar flow profile and wherein the diffusion regions are produced using silicone as a curable, liquid diffusion medium.

2. A light applicator according to claim 1, wherein the boundary surface is formed in a paraboloidal way between the diffusion regions.

3. A light applicator according to claim 1, whose diffusor comprises a mirror element at its distal end.

4. A light applicator according to claim 1, wherein the scattering probability increases towards the distal end due to the chosen scattering parameters in the diffusion regions.

5. A light applicator according to claim 4, wherein the concentration of scattering centers as averaged over the cross-sectional surface area increases along the optical axis towards the distal end of the diffusor.

6. A light applicator according to claim 1, whose diffusor has a homogeneous distribution of light along the optical axis as a result of the scattering parameters in the diffusion regions.

7. A light applicator according to claim 1, wherein the diffusor is associated with a reflection element by which the light emitted by the diffusor can be guided in predetermined directions.

8. A light applicator according to claim 7, wherein the reflection element is spherical segment which is applied on the diffusor and which is provided on one outer side with a layer reflecting the light.

9. A light applicator according to claim 7, wherein the transition between the light-emitting surface of the reflection element and the light-emitting surface of the diffusor has a conical nose.

10. A light applicator according to claim 7, wherein the distribution of the power density of the light emitted by the diffuser along the optical axis has a local maximum in the region of the reflection element as a result of chosen scattering parameters in the proximal diffusion regions.

11. A light applicator according to claim 10, wherein the concentration of the scattering centers as averaged over the cross section has a local maximum, in the region of the reflection element.

12. A light applicator according to claim 10, wherein the concentration of scattering centers along the optical axis as averaged over the cross-sectional surface area shows a minimum between the proximal end and the distal end of the diffusor.

13. A light applicator according to claim 7, wherein the distribution of light through the light-emitting surface of the reflections element and through the light-emitting surface of the diffusor is homogeneous.

14. A light applicator according to claim 1, wherein scattering particles present in the diffusion regions are $TiO_2$ or $BaSO_4$.

15. A light applicator according to claim 1, wherein the diffusion regions are enclosed by a covering which has a smaller refractive index than the refractive index of the diffusion regions.

16. A light applicator according to claim 1, whose light-emitting surfaces are covered by a partly backscattering layer.

17. A light applicator according to claim 1, whose diffusor's tube portion is flexible.

18. A light applicator according to claim 1, whose diffusor's tube portion is rigid.

19. A method for producing a diffusor/(light applicator), according to claim 1, which is connectable to a light guide and in which different diffusion regions with different scattering parameters are formed along an optical axis of the light guide prelongated into the diffusor, wherein:
   a hollow body is used for the diffusor which is filled at least in sections with a first diffusion medium,
   a second diffusion medium is injected into the first diffusion medium and
   in the first diffusion medium a boundary surface shaped according to a laminar flow profile is formed between the first diffusion medium and the second diffusion medium as a result of the laminar flow of the second diffusion medium in the first medium.

20. A method according to claim 19, wherein the boundary surface is formed in a paraboloidal way.

21. A method according to claim 19, wherein the first diffusion medium and the second diffusion medium are each sucked into the hollow body.

22. A method according to claim 19, wherein the second diffusion medium is injected from a first end of the hollow body into the first diffusion medium and a third diffusion medium is injected from a second end of the hollow body into the first diffusion medium.

23. A method according to claim 19, wherein the diffusion media are cured.

* * * * *